(12) United States Patent
Freilich et al.

(10) Patent No.: US 8,459,994 B2
(45) Date of Patent: Jun. 11, 2013

(54) IMMEDIATE IMPLANT SYSTEM

(76) Inventors: Martin A. Freilich, West Hartford, CT (US); A. Jon Goldberg, West Hartford, CT (US); Jonathan C. Meiers, Burlington, CT (US)

(*) Notice: Subject to any disclaimer, the term of this patent is extended or adjusted under 35 U.S.C. 154(b) by 2244 days.

(21) Appl. No.: 11/078,600

(22) Filed: Mar. 11, 2005

(65) Prior Publication Data

US 2005/0214717 A1 Sep. 29, 2005

Related U.S. Application Data

(60) Provisional application No. 60/552,182, filed on Mar. 11, 2004.

(51) Int. Cl.
*A61C 8/00* (2006.01)
*A61C 9/00* (2006.01)

(52) U.S. Cl.
USPC .......................................... 433/173; 433/214

(58) Field of Classification Search
USPC ............ 433/172–174, 214, 171, 167, 168.11, 433/169.1
See application file for complete search history.

(56) References Cited

U.S. PATENT DOCUMENTS

| | | | |
|---|---|---|---|
| 3,066,112 A | 11/1962 | Bowen | |
| 3,179,623 A | 4/1965 | Bowen | |
| 3,194,784 A | 7/1965 | Bowen | |
| 3,464,111 A * | 9/1969 | Gillard | 433/171 |
| 3,715,331 A | 2/1973 | Molnar | |
| 3,751,399 A | 8/1973 | Lee, Jr. et al. | |
| 3,926,906 A * | 12/1975 | Lee et al. | 523/116 |
| 4,019,253 A * | 4/1977 | Hazar | 433/71 |
| 4,479,527 A * | 10/1984 | Boettcher | 433/180 |
| 4,544,359 A | 10/1985 | Waknine | |
| 4,547,531 A | 10/1985 | Waknine | |
| 4,717,341 A | 1/1988 | Goldberg et al. | |
| 4,820,160 A * | 4/1989 | Cohen et al. | 433/229 |
| 4,894,012 A | 1/1990 | Goldberg et al. | |
| 5,015,183 A * | 5/1991 | Fenick | 433/173 |
| 5,276,068 A | 1/1994 | Waknine | |
| 5,444,104 A | 8/1995 | Waknine | |
| 5,684,103 A | 11/1997 | Jia et al. | |
| 5,927,980 A * | 7/1999 | Sillard | 433/173 |
| 6,013,694 A | 1/2000 | Jia et al. | |
| 6,186,791 B1 * | 2/2001 | Karmaker et al. | 433/220 |
| 6,322,364 B1 * | 11/2001 | Oshida et al. | 433/173 |
| 6,358,050 B1 | 3/2002 | Bergstrom et al. | |
| 6,358,052 B1 * | 3/2002 | Lustig et al. | 433/174 |

(Continued)

OTHER PUBLICATIONS

Press Release "FDA Clearance for Nobel Biocare's Teeth-in-an-Hour Implant System", Nobel Biocare Holding AG, Feb. 18, 2004 (p. 1 and p. 2).

*Primary Examiner* — Heidi M Eide
(74) *Attorney, Agent, or Firm* — Edwards Wildman Palmer LLP; Joshua L. Jones

(57) ABSTRACT

An implant system including a substructure, a suprastructure, abutments and an implant. The suprastructure is preferably fabricated of a light polymerized resin material having reinforcements such as fibers or fillers. The suprastructure is fabricated before the substructure. The use of resin materials that exhibit less shrinkage and the fact that the process begins with the suprastructure fabrication prevents distortion of the prosthesis when the suprastructure is bonded to the substructure and placed in the patient's mouth. Additionally, the method involved in making this implant system provides a prosthesis that is available to the patient almost immediately after surgery.

12 Claims, 6 Drawing Sheets
(6 of 6 Drawing Sheet(s) Filed in Color)

U.S. PATENT DOCUMENTS

| | | | |
|---|---|---|---|
| 6,402,517 B1 * | 6/2002 | Hozumi et al. | 433/173 |
| 6,655,962 B1 * | 12/2003 | Kennard | 433/174 |
| 6,666,684 B1 | 12/2003 | Names | |
| 2002/0039719 A1 * | 4/2002 | Honkura et al. | 433/189 |
| 2003/0134925 A1 * | 7/2003 | Guzauskas | 522/71 |
| 2003/0186197 A1 * | 10/2003 | Allred et al. | 433/226 |

* cited by examiner

IMMEDIATE IMPLANT SYSTEM

This application claims priority to and the benefits of U.S. Provisional Patent Application No. 60/552,182, filed on Mar. 11, 2004, the contents of which are incorporated herein in their entirety.

FIELD OF THE INVENTION

The present invention relates generally to an implant system and more specifically to a suprastructure of an implant system and the method of making the suprastructure and incorporating it into the implant system.

BACKGROUND OF THE INVENTION

Prostheses are connected to dental implants by attaching to an intermediary device that fits inside the implant. This device is called an abutment and it is generally placed into the implant between 6 and 12 weeks after implant surgery. Full arch prostheses connected to implant abutments are generally made with a metal substructure supporting a resin denture base material such as poly(methyl methacrylate) (PMMA) and artificial plastic teeth. The denture base and denture teeth comprise the prosthesis suprastructure. The metal alloys used for substructure fabrication exhibit very high rigidity. The metal substructure is able to resist overall distortion when the PMMA is added (polymerized) even though the PMMA exhibits very high polymerization shrinkage. However, among other concerns, metal alloys are unaesthetic and cannot form a chemical bond to the resin substructure materials. The use of fiber composite technology in the creation of a metal-free implant prosthesis may solve many of the problems associated with this metal alloy substructure such as corrosion, toxicity, complexity of fabrication, high cost and esthetic deficiencies. Prosthesis fabrication generally begins shortly after abutment placement. Due to the many steps and complexity of implant prosthesis fabrication, it usually takes weeks to months to complete. Therefore, the patient cannot benefit from the final implant prosthesis for an extended period of time.

Light polymerized glass fiber-reinforced composites (FRC)s have been developed that have the potential to make an esthetic implant prosthesis substructure utilizing a simple, time-efficient technique. Laboratory and clinical research evaluating FRC prostheses used to restore and replace teeth has shown that these materials exhibit excellent mechanical properties and can form a chemical bond to resin-based denture base materials. While the use of FRC materials for substructure fabrication offers important advantages over the use of metal alloy substructures, problems with this approach have been identified. Laboratory testing has shown that FRC materials used to make the prosthesis substructure exhibit very little polymerization shrinkage resulting in excellent dimensional stability of the substructure with no apparent misfit at implant abutment interface areas. However, FRC materials are not as rigid as metal alloys. Consequently, laboratory testing has also shown that the polymerization of PMMA denture base material with embedded denture teeth over this dimensionally stable FRC substructure results in measurable distortion due to the expected high polymerization shrinkage of the PMMA.

This finding was a great concern. From the data obtained in the laboratory and clinical studies, the inventors determined that there was measurable error in the dimensions of the prosthesis when the PMMA denture base and denture teeth were polymerized to the substructure using a standard heat processing technique. This technique is typical for the fabrication of complete dentures or during the placement of PMMA on removable partial dentures or metal supported full arch implant prostheses.

A noteworthy prosthesis misfit should result in "rocking" or lack of stability of the prosthesis when placed in the mouth and an increased likelihood of screw loosening after prosthesis placement. Tightening the fastening screws that attach the prosthesis to the abutments can generally eliminate the slight misfit observed at the prosthesis/abutment interface. While the tightening of the prosthesis fastening screws eliminates any misfit at the abutment/cylinder interface, this may result in high internal strain within the prosthesis, likely at the suprastructure/substructure interface. Consequently, there is potential for long-term clinical problems due to prosthesis distortion upon suprastructure polymerization.

Additional problems associated with implant prostheses are the breakage and debonding of denture teeth with clinical usage. There is much evidence that this is a universal problem associated with full arch implant prostheses regardless of whether metal alloy or FRC are used for the substructure material. Denture teeth were designed and manufactured to be placed on removable prostheses. Patients are unable to place high loads on these removable prostheses due to their soft tissue support. Also, denture teeth bond poorly to the PMMA that they are placed into. This results in the need to place mechanical retention into the underside of the denture teeth, which further compromises their strength. This is the case for all implant prostheses, not just FRC implant prostheses.

There is a need to provide strong denture teeth to withstand the stresses in a patient's mouth. It would also be beneficial to provide a bonding mechanism to enable denture teeth to adhere strongly to the denture base without the need to grind or machine the teeth to create mechanical retention. It would be advantageous to minimize or eliminate full arch FRC implant prosthesis distortion. It would certainly be preferable to provide a prosthesis for attachment to implants in a time period shortly or immediately following surgical placement of the implants in a patient's mouth.

SUMMARY OF THE INVENTION

These and other objects and advantages are accomplished by the implant system of the present invention comprising a substructure, a suprastructure, abutments and an implant. The suprastructure is preferably fabricated of a light polymerized resin material having reinforcements such as fibers or fillers. The suprastructure is fabricated before the substructure. The suprastructure can include denture teeth and a denture base. A first resin can be used to make the denture teeth and a second resin can be used to make the denture base. A third resin can be used to make the substructure. A resin having the same or similar functional group can be used for the first resin, second resin, third resin and adhesive resin. The use of resin materials that exhibit less shrinkage and the fact that the process begins with the suprastructure fabrication prevents distortion of the prosthesis when the suprastructure is bonded to the substructure and placed in the patient's mouth. Additionally, the method of making this implant system provides a prosthesis that is available to the patient almost immediately after surgery.

BRIEF DESCRIPTION OF THE DRAWINGS

Features of the present invention are disclosed in the accompanying drawings, wherein similar reference characters denote similar elements throughout the several views, and wherein.

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
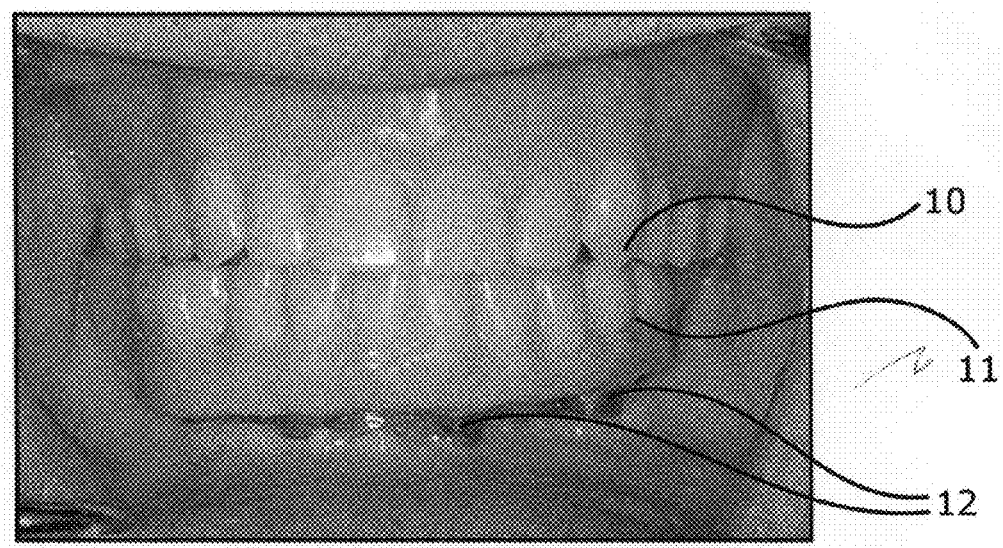
FIG. 1 is a front perspective view of an implant system in accordance with the invention placed in a patient's mouth.

As will be appreciated, the present invention provides an implant system that contains a substructure, a suprastructure, abutments and an implant. Reference is made to FIG. 1 which shows the finished implant system 10 placed in the patient's mouth comprising prosthesis 11 and implant abutments 12. Prosthesis 11 contains a suprastructure 14 (FIG. 4) and a substructure 24 (FIG. 9) to be further described and discussed.

Figure 2:
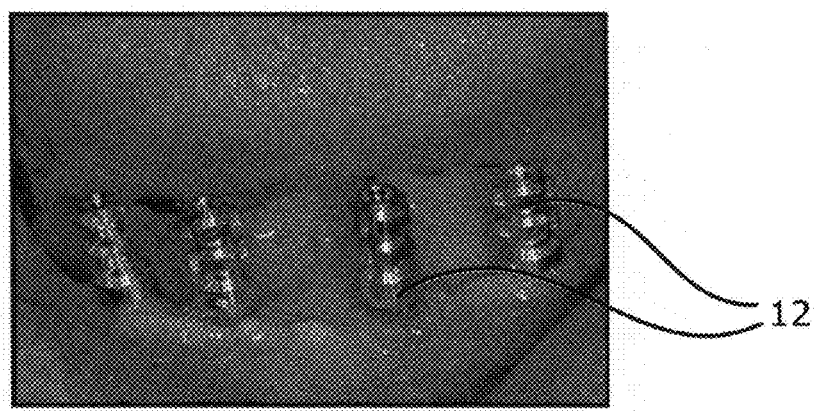
FIG. 2 is a front perspective view of abutments placed in implants in a patient's mouth.
Figure 3:
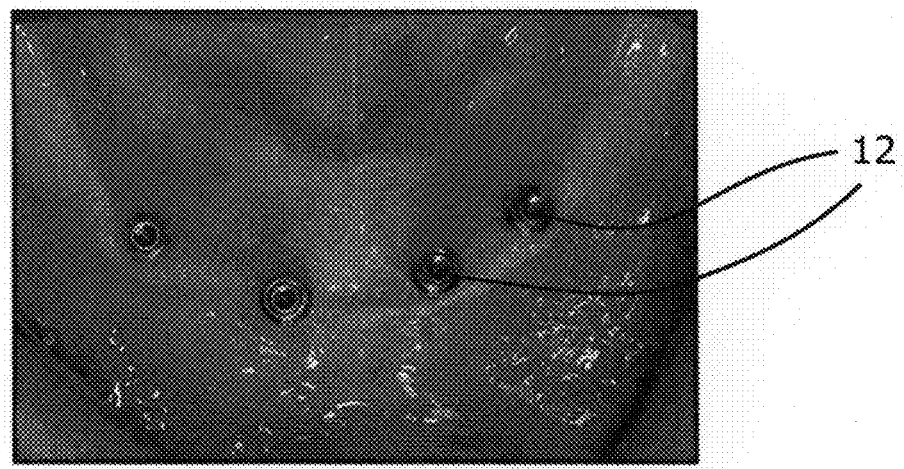
FIG. 3 is a top perspective view of FIG. 2.
Figure 4:
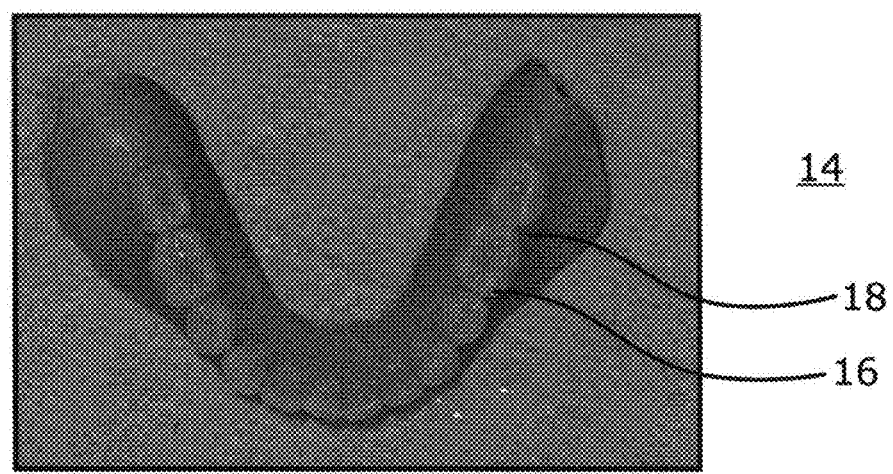
FIG. 4 is a top perspective view of a suprastructure in accordance with the invention.

FIGS. 2 and 3 show abutments 12 of the implant system placed into the implants located in the patient's mouth. Prior to the surgical placement of the implants, suprastructure 14, shown in FIG. 4, is fabricated. The inventors herein describe this as the "outside in" approach, since this process differs from standard procedures used to manufacture implant prostheses. Instead of inserting the abutments in the patient's mouth, fabricating the substructure that attaches to the abutments, followed by fabricating the suprastructure that attaches to the substructure, this invention first begins with the step of suprastructure fabrication.

Suprastructure 14 is in the shape of a complete denture and includes teeth 16 and denture base material 18. Denture base material 18 and teeth 16 of suprastructure 14 may be fabricated of metal, plastic, ceramic, polymeric material or a mixture thereof, similar to those materials used to make standard denture base materials and those materials used to fabricate standard composite restorative materials. Examples of these materials include thermoset and thermoplastic materials, which include but are not limited to, poly(methyl methacrylate), poly(ethyl methacrylate), poly(butyl methacrylate), polyamides, polyesters, polyolefins, polyimides, polyarylates, polyacrylates, polyurethanes, vinyl esters, epoxy-based materials, styrenes, stryrene acrylonitriles, ABS polymers, polysulfones, polyacetals, polycarbonates, polyphenylene sulfides, and the like.

Preferred polymeric materials in the composite include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; U.S. Pat. Nos. 5,276,068 and 5,444,104 to Waknine; and U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), urethane dimethacrylate (hereinafter abbreviated "UDMA"), hexane diol dimethacrylate (hereinafter abbreviated "1,6 HDDMA") and polycarbonate dimethacrylate (hereinafter abbreviated "PCDMA") are also commonly-used principal polymers suitable for use in the present invention.

It is preferable that denture base material 18 and teeth 16 are fabricated of a reinforced composite polymeric or resinous material and more preferably, a light polymerizable reinforced composite material reinforced with a small amount of reinforcing agent.

The amount of reinforcing component present in the polymeric matrix may depend on the transition temperature (Tg) of the resin. If the Tg is above room temperature (about 20-25° C. or about 68-77° F.), the amount of filler added may be in an amount of about 5% to about 40% by weight, preferably about 3% to 25% by weight and most preferably up to about 10% by weight. If the Tg is below room temperature (about 20-25° C. or about 68-77° F.), the amount of filler added may be in an amount up to about 70% by weight, preferably about 5% to about 60% by weight and most preferably about 10% to about 20% by weight.

The reinforcing component includes, but is not limited to, fibers, fillers, powders, particulate and mixtures thereof. Examples of the reinforcing component include, but are not limited to, fillers that are capable of being covalently bonded to the polymeric matrix itself or to a coupling agent that is covalently bonded to both. Examples of suitable filling materials include but are not limited to those known in the art such as silica, silicate glass, quartz, barium silicate, barium sulfate, barium molybdate, barium methacrylate, barium yttrium alkoxy ($Ba_2Y(OR)_x$), strontium silicate, barium borosilicate, strontium borosilicate, borosilicate, lithium silicate, amorphous silica, ammoniated or deammoniated calcium phosphate and alumina, zirconia, tin oxide, tantalum oxide, niobium oxide, and titania. Particularly suitable fillers for dental filling-type materials prepared in accordance with this invention are those having a particle size ranging from about 0.1-5.0 microns with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. Nos. 4,544,359 and 4,547,531 to Waknine, the pertinent portions of which are incorporated herein by reference. Suitable organic filler materials are known in the art, including for example the poly(methacrylate) fillers described in U.S. Pat. No. 3,715,331 to Molnar. A mixture of organic and inorganic filler materials may also be used.

The reinforcing fiber element of the composite preferably comprises glass, carbon, graphite, polyaramid, polyethylene, or other fibers known in the art, such as polyesters, polyamides, and other natural and synthetic materials compatible with the polymeric matrix. Some of the aforementioned fibrous materials and fillers materials are disclosed in U.S. Pat. Nos. 6,013,694, 4,717,341 and 4,894,012 all of which are incorporated herein by reference. The fibers may further be treated, for example, chemically or mechanically etched, silanized, or otherwise treated such as by grafting functional monomers to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, NY.

The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the strip. However, depending on the end use of the composite material, the fibers may also be otherwise oriented, including being normal or perpendicular to that dimension. The fibrous element may optionally take the form of a fabric. Fabric may be of the woven or non-woven type and is preferably preimpregnated with a polymeric material as set forth above. The fibrous component may be present in the fiber reinforced composite material in the range from about 20% to about 85% of the composite, and more preferably between about 30% to about 65% by weight.

The polymeric matrix in the reinforced composite may also include polymerization initiators, polymerization accelerators, ultraviolet light absorbers, anti-oxidants, and other additives well known in the art. The polymeric matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis(cyclohexanecarbo-nitrile), or other free radical initiators. The preferred polymeric matrix is a curable matrix, wherein light cure effects partial cure of the matrix, and final curing is by heat under controlled atmosphere or alternatively, the preferred matrix is a light curable matrix which is completely cured by light alone.

Use of light polymerizable resin materials makes it possible to fabricate denture base material 18 in segments as opposed to fabricating the entire base at one time, as when heat polymerized polymethylmethacrylate (PMMA) materials are used. It is preferable that the denture base be fabricated of materials having some type of reinforcement material dispersed therein including but not limited to fillers, fibers or a combination thereof, to increase the strength and reliability of the components. Base material 18 is easy to handle and bonds well to the substructure beneath it and to the denture teeth placed into it.

Using a light polymerized resin material reduces the polymerization shrinkage of the suprastructure due to the ability of the technician to place and polymerize the material in segments during the fabrication thereof. Each segment compensates for the shrinkage of the previous segment. Addition of light polymerized, low shrinkage resins to attach the substructure to the already polymerized suprastructure results in little or no prosthesis distortion prior to placement in the patient's mouth.

In order to strongly bond the denture teeth to the denture base material, the materials may be mechanically or chemically etched or abraded to provide good adhesive surfaces. The denture base material may include a low viscosity component that is able to wet the treated denture tooth surface resulting in optimal micromechanical retention. Improved bonding between the denture teeth and the base material eliminates the need to place (with a tool such as a bur) macro mechanical retentive features, such as a hole, to the undersurface of the denture teeth. These retentive features have the potential to further weaken the denture tooth and exacerbate the denture tooth strength problem.

Figure 5:
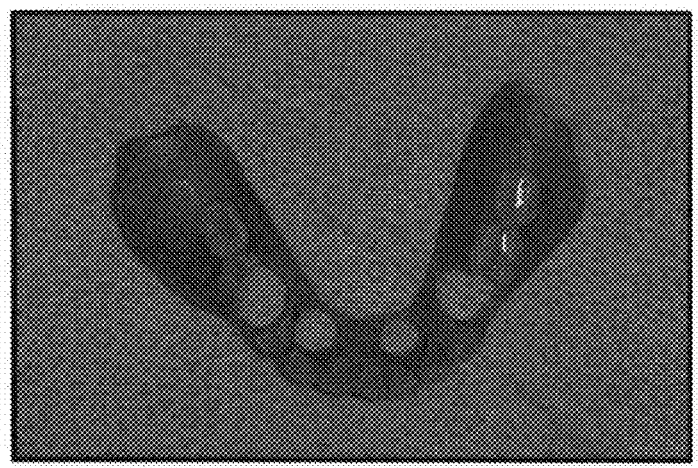
FIG. 5 is a top perspective view of a hollowed out suprastructure in accordance with the invention.
Figure 6:
FIG. 6 is a top plan view of a bite registration in accordance with the invention.

After fabrication of suprastructure 14, it is hollowed out as shown in FIG. 5. Suprastructure 14 is then tried in the patient's mouth to verify the occlusal relationship prior to implant surgery. A bite registration 20, shown in FIG. 6, is made between suprastructure 14 and the opposing arch in the patient's mouth.

Figure 7:
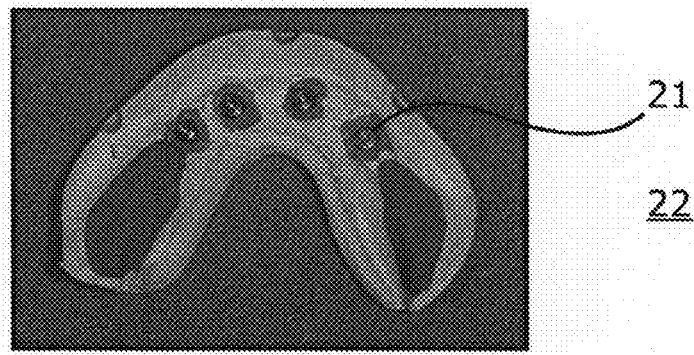
FIG. 7 is a top plan view of a master cast in accordance with the invention.

Next, implants 12 are inserted into the patient's mouth and suprastructure 14 is used as an impression tray to record the position of the newly placed implants. Implant analogs 21 are placed in the impression to mimic the position of the implants in the mouth and a master cast 22 with analogs 21 positioned therein, shown in FIG. 7, is made from this impression.

Figure 8:
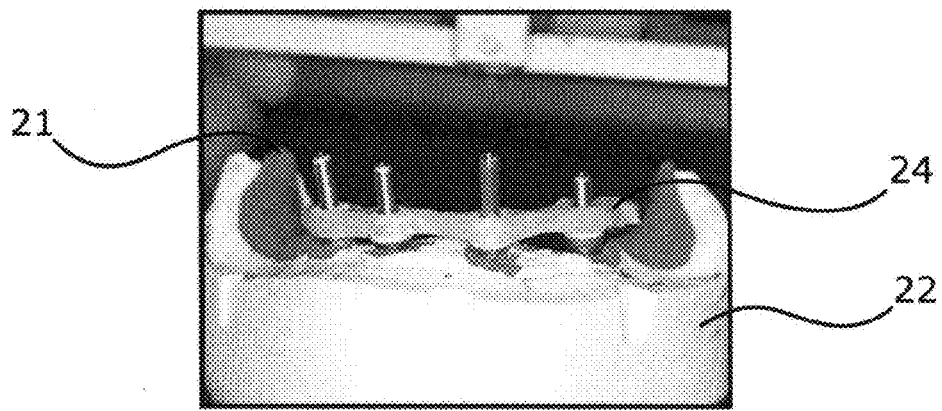
FIG. 8 is a front perspective view of a substructure in accordance with the invention.
Figure 9:
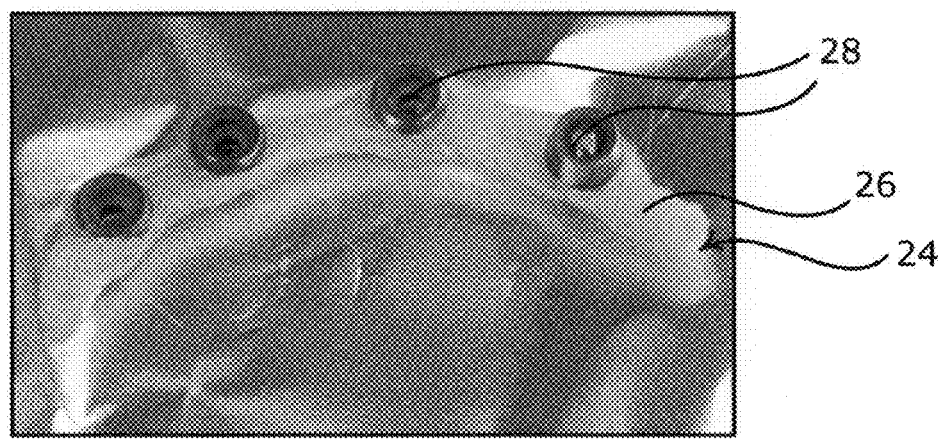
FIG. 9 is a top perspective view of a substructure in accordance with the invention.

A substructure 24, shown in FIG. 8, is fabricated on master cast 22. A bottom plan view of substructure 24 is shown in FIG. 9, wherein substructure 24 is fabricated of fiber reinforced composite material 26 wrapped and built around cylinders 28. Examples of materials used for fabricating the fiber reinforced composite material framework 26 and cylinders 28 are described in copending application U.S. Ser. No. 09/311,464, filed May 13, 1999, which is hereby incorporated by reference. The substructure is the framework of the implant system and connects to the implant components that are implanted into a patient's mouth. It also is bonded or connected to the suprastructure and supports the suprastructure. Cylinders 28 connect to the implants and framework 26 that is formed on cylinders 28 provides a structure on which suprastructure 14 bonds. Cylinders 28 may be fabricated of any known material such as metal, plastic, ceramic, polymeric material and mixtures thereof. One example of cylinders useful herein are machined titanium metal cylinders that are sprayed with a special titanium compatible ceramic, which via a resin/ceramic interface, are connected to and surrounded by pre-impregnated, unidirectional FRC material.

Figure 10:
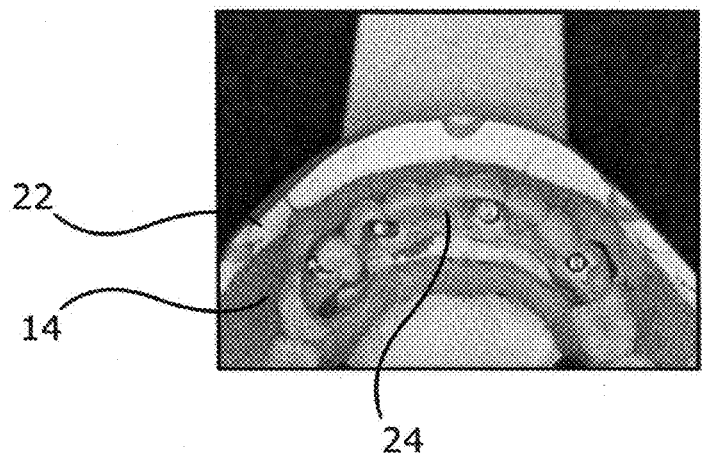
FIG. 10 is a top plan view of substructure and suprastructure positioned on the master cast in accordance with the invention.
Figure 11:
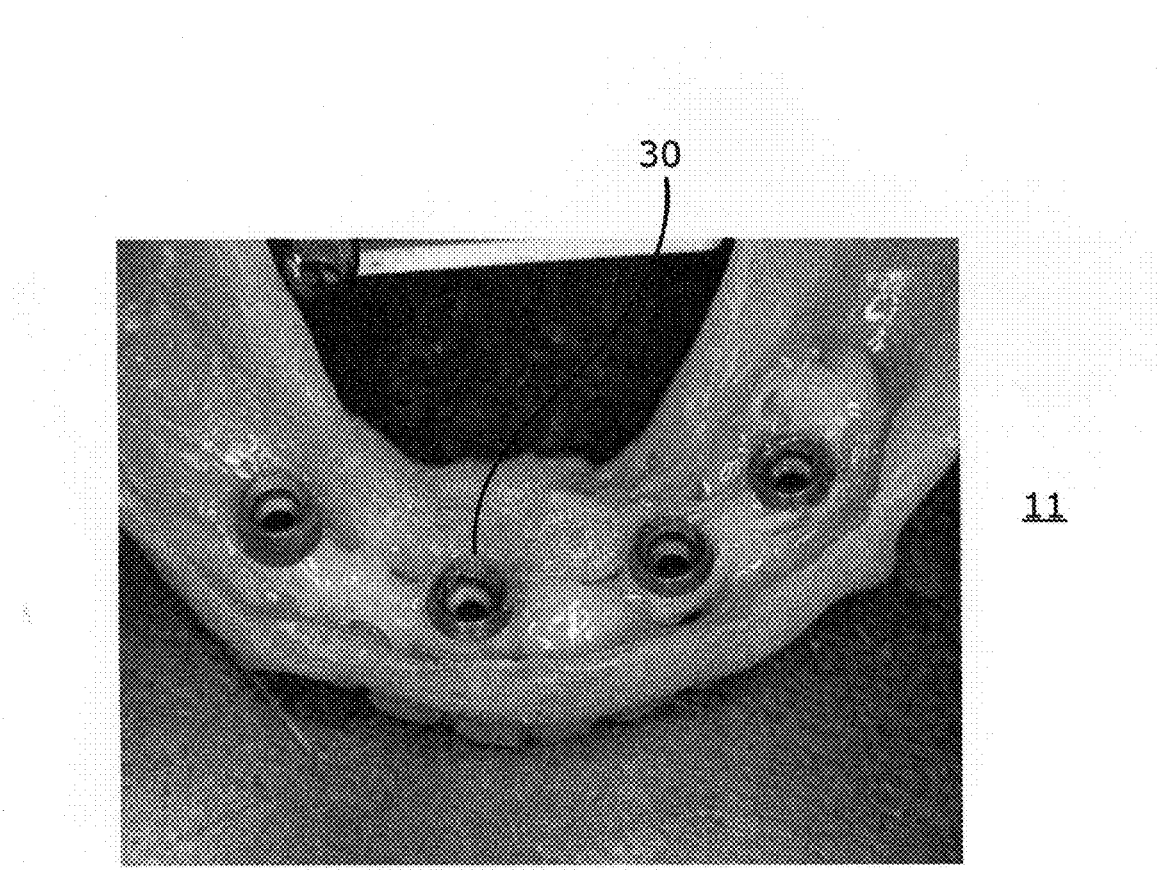
FIG. 11 is a top perspective view of a prosthesis in accordance with the invention.

In FIG. 10, suprastructure 14 is shown repositioned over master cast 22 having fiber reinforced composite substructure 24 thereon. As shown in FIG. 11, an adhesive material 30 is placed between substructure 24 and suprastructure 14 in order to bond substructure 24 to suprastructure 14 resulting in prosthesis 11. It is preferable that adhesive material 30 is the same material used to fabricate denture base material 18 or at least has the same or similar functional group as denture base material 18 to provide a covalent or chemical bond between the materials. It is further preferable that adhesive material 30 and the resins used to make substructure 24 and suprastructure 14 have the same or similar functional group to provide a covalent or chemical bond between the materials. It is further preferable that substructure 24 has an air-inhibited layer on its exterior and that suprastructure 14 has an air-inhibited layer on the inner surface so that adhesive material 30 easily bonds to both structures. The resulting prosthesis 11 having suprastructure 14 and substructure 24 bonded together with base material 30 is shown in FIG. 11. This almost immediate approach is feasible because the suprastructure is made prior to surgery and once the orientation of the implants can be recorded in the master cast, a substructure can be made and bonded to the already-made suprastructure. Prosthesis 11 is now ready for attachment to the implant abutments 12 located in the patient's mouth.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of making an implant system comprising:
   making a suprastructure;
   fitting the suprastructure in the patient's mouth to make a bite registration between the suprastructure and the opposing arch;
   using the suprastructure as an impression tray to record the position of implants in a patient's mouth and to provide an impression of the implants;
   using the impression to make a master cast having implant analogs;
   making a substructure using the master cast;
   positioning the suprastructure on the substructure; and
   applying adhesive resin between the suprastructure and the substructure to bond the suprastructure to the substructure.

2. The method of making an implant system of claim 1 comprising making the substructure and suprastructure of metal, plastic, ceramic, polymeric material or a combination thereof.

3. The method of making an implant system of claim 2 comprising using filler or fiber reinforced composite material as the polymeric material to make the substructure and suprastructure.

4. The method of making an implant system of claim 1 comprising making the suprastructure comprising denture teeth and a denture base.

5. The method of making an implant system of claim 4 comprising using a first resin to make the denture teeth and a second resin to make the denture base.

6. The method of making an implant system of claim 5 comprising using a third resin to make the substructure.

7. The method of making an implant system of claim 6 comprising using a resin having the same or similar functional group for the first resin, second resin, third resin and adhesive resin.

8. The method of making an implant system of claim 4 wherein the denture teeth and denture base are mechanically or chemically etched or abraded to provide a good adhesive surface.

9. The method of making an implant system of claim 1 comprising forming air-inhibited layers on the suprastructure and substructure to enhance the bond with the adhesive resin.

10. The method of making an implant system of claim 1 comprising making the substructure with a fiber-reinforced composite framework wrapped around cylinders fabricated of metal, plastic, ceramic, polymeric material or a mixture thereof.

11. The method of making an implant system of claim 10 comprising making the cylinders of titanium metal coated with a titanium-compatible ceramic.

12. The method of making an implant system of claim 1 wherein the adhesive resin comprises a low viscosity resin.

* * * * *